United States Patent
Kim et al.

(10) Patent No.: US 7,085,599 B2
(45) Date of Patent: Aug. 1, 2006

(54) CHARACTERIZATION OF SUPRAVENTRICULAR RHYTHM USING COLLECTED CARDIAC BEATS

(75) Inventors: Jaeho Kim, Redmond, WA (US); Joseph Bocek, Seattle, WA (US)

(73) Assignee: Cardiac Pacemakers, Inc., St. Paul, MN (US)

(*) Notice: Subject to any disclaimer, the term of this patent is extended or adjusted under 35 U.S.C. 154(b) by 544 days.

(21) Appl. No.: 10/278,746

(22) Filed: Oct. 23, 2002

(65) Prior Publication Data

US 2004/0082973 A1    Apr. 29, 2004

(51) Int. Cl.
  *A61B 5/0452* (2006.01)
(52) U.S. Cl. .................. 600/509; 600/515; 600/517
(58) Field of Classification Search .............. None
  See application file for complete search history.

(56) References Cited

U.S. PATENT DOCUMENTS

| | | | |
|---|---|---|---|
| 5,000,189 A | 3/1991 | Throne et al. ............. 600/515 |
| 5,217,021 A | 6/1993 | Steinhaus et al. .......... 600/515 |
| 5,447,519 A | 9/1995 | Peterson ...................... 607/5 |
| 5,645,070 A * | 7/1997 | Turcott ........................ 600/515 |
| 5,779,645 A | 7/1998 | Olson et al. ................. 600/518 |
| 5,817,027 A | 10/1998 | Arand et al. ................ 600/515 |
| 5,857,977 A | 1/1999 | Caswell et al. |
| 6,035,232 A | 3/2000 | Thong et al. ................ 600/510 |
| 6,052,620 A | 4/2000 | Gillberg et al. .............. 607/4 |
| 6,067,471 A | 5/2000 | Warren ........................ 607/5 |
| 6,076,014 A | 6/2000 | Alt ............................... 607/4 |
| 6,449,503 B1 * | 9/2002 | Hsu ............................. 600/518 |
| 6,470,210 B1 * | 10/2002 | Chen et al. .................. 600/515 |
| 6,671,548 B1 * | 12/2003 | Mouchawar et al. ........ 607/14 |
| 6,745,068 B1 * | 6/2004 | Koyrakh et al. ............ 600/515 |
| 2002/0193695 A1 * | 12/2002 | Koyrakh et al. ............ 600/510 |
| 2004/0019287 A1 * | 1/2004 | White ........................... 600/509 |

* cited by examiner

*Primary Examiner*—Carl Layno
(74) *Attorney, Agent, or Firm*—Hollingsworth & Funk, LLC

(57) ABSTRACT

The supraventricular rhythm of a patient's heart is characterized using cardiac beats collected during a plurality of time periods, some of which are noncontiguous. Pacing parameters may be modified to allow the development of a spontaneous rhythm. Waveforms of the collected cardiac beats are stored for later processing, or are combined with previously collected beats and the combination is stored. When a sufficient number of cardiac beats are collected, the patient's supraventricular rhythm is characterized using the collected cardiac beats.

38 Claims, 13 Drawing Sheets

CHARACTERIZATION OF SUPRAVENTRICULAR RHYTHM USING COLLECTED CARDIAC BEATS

FIELD OF THE INVENTION

The present invention relates generally to implantable medical devices and, more particularly, to generating, with an implantable medical device, a characterization of a patient's supraventricular rhythm using cardiac beats collected while the heart is intermittently or consistently paced.

BACKGROUND OF THE INVENTION

The healthy heart produces regular, synchronized contractions. Rhythmic contractions of the heart are normally controlled by the sinoatrial (SA) node, specialized cells located in the upper right atrium. The SA node is the normal pacemaker of the heart, typically initiating 60–100 heart beats per minute. When the SA node is pacing the heart normally, the heart is said to be in normal sinus rhythm (NSR).

If heart contractions are uncoordinated or irregular, the heart is denoted to be arrhythmic. Cardiac arrhythmia impairs cardiac efficiency and can be a potential life threatening event. Cardiac arrhythmias have a number of etiological sources including tissue damage due to myocardial infarction, infection, or degradation of the heart's ability to generate or synchronize the electrical impulses that coordinate contractions.

Bradycardia occurs when the heart rhythm is too slow. This condition may be caused, for example, by delayed impulses from the SA node, denoted sick sinus syndrome, or by a blockage of the electrical impulses between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid, uncoordinated contractions of the atria. Besides being hemodynamically inefficient, the rapid contractions of the atria can also adversely affect the ventricular rate. This occurs when the aberrant contractile impulses in the atria are transmitted to the ventricles. It is then possible for the aberrant atrial signals to induce ventricular tachyarrhythmias.

Ventricular tachycardia occurs, for example, when a pulse is initiated in the ventricular myocardium at a rate more rapid than the normal sinus rhythm. Ventricular tachycardia can quickly degenerate into ventricular fibrillation (VF). Ventricular fibrillation is a condition denoted by extremely rapid, nonsynchronous contractions of the ventricles. The rapid and erratic contractions of the ventricles cannot effectively pump blood to the body and the condition is fatal unless the heart is returned to sinus rhythm within a few minutes.

Implantable cardiac rhythm management systems have been used as an effective treatment for patients with serious arrhythmias. These systems typically comprise circuitry to sense signals from the heart and a pulse generator for providing electrical stimulation to the heart. Leads extending into the patient's heart are connected to electrodes that contact the myocardium for sensing the heart's electrical signals and for delivering pulses to the heart in accordance with various therapies for treating the arrhythmias described above.

Pacemakers are cardiac rhythm management systems that deliver pace pulses to the heart. Pace pulses are low energy electrical pulses timed to assist the heart in producing a contractile rhythm that maintains cardiac pumping efficiency. Pace pulses may be intermittent or consistent, depending on the needs of the patient. There exist a number of categories of pacemaker devices, with various modes for sensing and pacing the heart. Single chamber pacemakers pace and sense one heart chamber. A typical single chamber pacemaker is connected to one lead extending either to the right atrium or the right ventricle. Dual chamber pacemakers may pace and sense two chambers of the heart. A typical dual chamber pacemaker is typically connected to two leads, one lead extending to the right atrium and one lead to the right ventricle. Pacemakers can be programmed to provide pace pulses to the heart on demand or at a fixed rate.

When a pacemaker paces the heart at a fixed rate, the pacemaker provides pace pulses to the heart without taking into account the heart's spontaneous action. In contrast, pacemakers that provide pacing pulses on demand sense the spontaneous activity of the heart and provide pace pulses synchronized to the spontaneous activity. For example, a single chamber ventricular pacemaker may sense and pace a ventricle. The pacemaker senses ventricular activity and provides a pace pulse to the ventricle if no spontaneous activity is sensed. If the pacemaker senses spontaneous activity, the pacing pulse is inhibited. Alternatively, a single chamber pacemaker may sense and pace the atrium. A dual chamber pacemaker may be capable, for example, of sensing and pacing both the atrium and ventricle. The dual chamber pacemaker may be capable of using pace pulses to synchronize atrial and ventricular activity. If spontaneous cardiac activity is detected in the atrium or the ventricle, pacing pulses may be inhibited or triggered.

Implantable cardioverter/defibrillators (ICDs) have been used as an effective treatment for patients with serious tachyarrhythmias. ICDs are capable of delivering high energy shocks to the heart, interrupting the tachyarrhythmia or fibrillation and allowing the heart to resume a normal rhythm. ICDs may include pacing functions described above as well as cardioversion/defibrillation capabilities.

To effectively provide treatment, a cardiac rhythm management system, such as an ICD or pacemaker, must identify the type of arrhythmia that is occurring and provide appropriate therapy to the heart. Arrhythmias may be identified by comparing the aberrant rhythm to a supraventricular rhythm. For the reasons stated above, and for other reasons that will become apparent to those skilled in the art upon reading the present specification, there is a need in the art for a method and system that reliably and accurately characterizes a patient's supraventricular rhythm when the heart is being intermittently or consistently paced. The present invention fulfills these and other needs.

SUMMARY OF THE INVENTION

The present invention is directed to a method and system for characterizing an EGM of one beat of a patient's supraventricular cardiac rhythm (SVR) while the heart is being intermittently or consistently paced. In accordance with one embodiment of the present invention, a method for characterizing a patient's supraventricular rhythm involves collecting cardiac beats representative of the patient's supraventricular rhythm during a plurality of periods, of which some are noncontiguous. The patient's supraventricular rhythm is characterized using the collected beats.

In another embodiment of the invention, a system for characterizing a patient's supraventricular rhythm includes a lead system, a detector system, and control system. The lead system comprises electrodes extending into the patient's heart. The detector system is coupled to the lead system and is configured to detect cardiac beats. The control system is coupled to the lead system and the detector system. The control system is configured to control the pacing of the patient's heart, collect cardiac beats representative of the patient's supraventricular rhythm during a plurality of periods, some of which are noncontiguous, and characterize the patient's supraventricular rhythm using the collected beats.

Yet another embodiment of the invention includes means for collecting cardiac beats during a plurality of periods, of which some are noncontiguous, and means for characterizing the patient's supraventricular rhythm using the collected cardiac beats.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
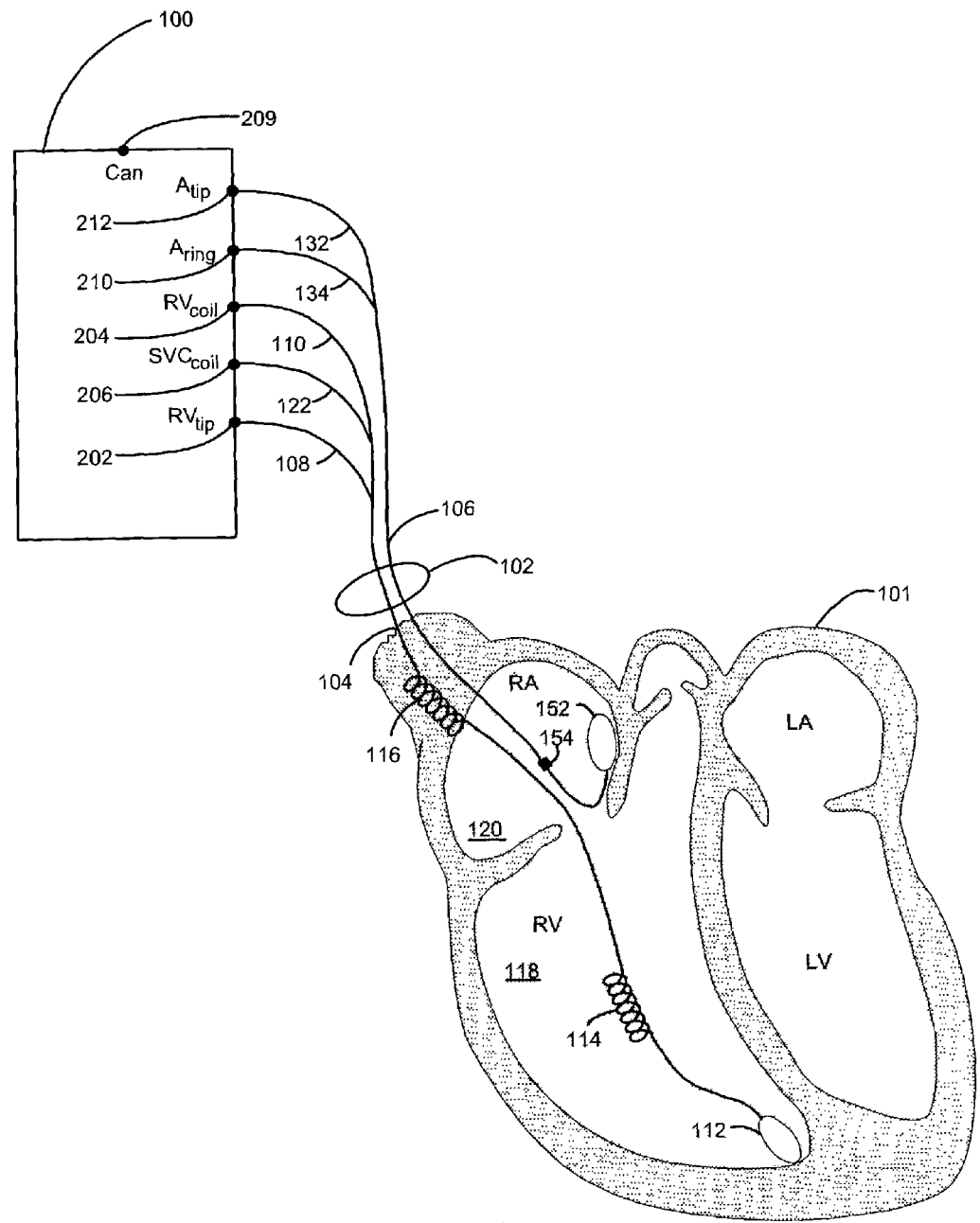
FIG. 1 is a partial view of one embodiment of a dual chamber implantable medical device with an endocardial lead system extending into atrial and ventricular chambers of a heart.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

A proper characterization of a patient's supraventricular rhythm requires detection of unpaced or intrinsic heartbeats. Although various methods have been proposed for characterizing a patient's supraventricular rhythm, these characterization methods are often dependent upon acquiring a sufficient number of intrinsic beats during a particular time interval. One such method is described in commonly owned U.S. patent application Ser. No. 09/845,987, filed Apr. 30, 2001, and entitled "Normal Cardiac Rhythm Template Generation System and Method," (1275.4US01), which is hereby incorporated herein by reference. Another method is described in commonly owned U.S. patent application Ser. No. 10/105,875, filed Mar. 25, 2002, and entitled "Method and System for Characterizing a Representative Cardiac Beat Using Multiple Templates," (GUID.041US01), which is incorporated herein by reference. Yet another method is described in commonly owned U.S. patent application Ser. No. 10/121,944, filed Apr. 12, 2002 and entitled "Method and System For Characterizing Supraventricular Rhythm During Cardiac Pacing," (GUID.040PA), which is incorporated herein by reference.

Notwithstanding the efficacy of these approaches, additional processes may be required to obtain a characterization of supraventricular rhythm (SVR) when the heart is being intermittently or consistently paced. Paced beats are not considered intrinsic beats and generally cannot be used to characterize supraventricular rhythm. Consequently, when the heart is being paced, intrinsic beats may not be available for SVR characterization by previous methods.

The invention described herein provides a method and system for characterizing supraventricular rhythm for patients requiring intermittent or consistent pacing. Various embodiments of the present invention include collecting cardiac beats representative of the patient's supraventricular conducted rhythm during a number of intervals, some of which are noncontiguous. A beat may be collected by storing the beat waveform. Alternatively, or additionally, the beat may be collected by combining the beat with previously collected beats and storing the result of the combination. The patient's supraventricular rhythm may be characterized after a predetermined number of SVR-representative beats have been collected.

According to one aspect of the invention, a pacing parameter may be periodically modified to elicit intrinsic beats during a number of intervals. If the elicited intrinsic beats are representative of the patient's supraventricular rhythm, the beats are collected and stored. The patient's supraventricular rhythm is characterized after a predetermined number of beats have been stored.

The embodiments of the present system illustrated herein are generally described as being implemented in an implantable cardiac defibrillator (ICD), which may operate in numerous pacing modes known in the art. The systems and methods of the present invention may also be implemented in other implantable or external medical devices that sense cardiac activity, such as pacemakers, cardiac monitors, and resynchronizers, for example.

Various types of single and multiple chamber cardiac rhythm management systems are known in the art. In one embodiment, the cardiac rhythm management system is implemented as an implantable cardiac defibrillator configured as a dual chamber device that operates to generate a characterization of one beat of a patient's supraventricular rhythm in accordance with the principles of the present invention. The systems and methods of the present invention may also be implemented in external cardioverter/monitor systems as are known in the art. Also, the methods of the present invention may be implemented in an implantable atrial rhythm management system, which may include numerous pacing modes known in the art. Furthermore, methods of the present invention may be implemented in a bi-ventricular or bi-atrial device. Although the present system is described in conjunction with an implantable cardioverter/defibrillator (ICD) having a microprocessor-based architecture, it will be understood that the cardiac rhythm management system may be implemented in any logic-based integrated circuit architecture, if desired.

Characterization of supraventricular rhythm requires collection of a sufficient number of intrinsic beats. However, when the heart is being intermittently or consistently paced, intrinsic beats are not produced, or are only occasionally produced. Therefore, SVR characterization when the heart is being paced may not be possible using previous methods. The present invention provides a method and system for monitoring a patient's electrocardiogram and producing a characterization of the patient's supraventricular rhythm while the heart is being intermittently or consistently paced.

Producing such a characterization may be effected for a number of different purposes. By way of example, the diagnosis of a patient's cardiac rhythms may be enhanced by comparing QRS complexes of a current cardiac rhythm to a characterization of the patient's supraventricular rhythm produced by employment of the methodologies of the present invention. By way of further example, the titration of drug dosage based on a comparison of cardiac complexes to a characterization of supraventricular rhythm produced in accordance with the present invention may also be enhanced.

The methods of producing a characterization of a patient's supraventricular cardiac rhythm may be used in combination with various cardiac rhythm management techniques, such as, for example, an automatic VT/SVT (ventricular tachyarrhythmia/supra-ventricular tachyarrhythmia) rhythm discrimination technique employed in an implantable cardioverter/defibrillator (ICD). Also, the methodologies of the present invention may be used as a component of an automatic Holter analysis employed in an implantable pacemaker, for example. These and other applications may be enhanced by employment of the systems and methods of the present invention.

FIG. 1 shows one embodiment of a cardiac rhythm management system that includes an implantable cardioverter/defibrillator (ICD) 100 electrically and physically coupled to an intracardiac lead system 102. The intracardiac lead system 102 is implanted in a human body with portions of the intracardiac lead system 102 inserted into a heart 101. The intracardiac lead system 102 is used to detect and analyze electric cardiac signals produced by the heart 101 and to provide electrical energy to the heart 101 under predetermined conditions to treat cardiac arrhythmias of the heart 101. The electrical energy provided may be in the form of low energy pacing pulses or high energy pulses for cardioversion or defibrillation. The ICD 100 depicted in FIG. 1 is a dual chamber device, capable of sensing signals from the right atrium and right ventricle and providing pacing pulses or cardioversion/defibrillation pulses to the right atrium and the right ventricle. In an embodiment in which only pacing is performed, the ICD 100 need not provide for generation of high energy pulses.

The intracardiac lead system 102 includes a right ventricular lead system 104 and a right atrial lead system 106. The right ventricular lead system 104 includes an SVC-coil 116, an RV-coil 114, and an RV-tip electrode 112. The atrial lead system 106 includes an A-tip electrode 152 and an A-ring electrode 154. In one embodiment, the atrial lead system 106 is configured as an atrial J lead.

In the configuration of FIG. 1, the intracardiac lead system 102 is positioned within the heart 101, with a portion of the atrial lead system 106 extending into the right atrium 120 and portions of the right ventricular lead system 104 extending through the right atrium 120 into the right ventricle 118. The A-tip electrode 152 and A-ring electrode 154 are positioned at appropriate locations within the right atrium 120. The RV-tip electrode 112 and RV-coil 114, which may also be configured as a ring electrode, are positioned at appropriate locations within the right ventricle 118. The SVC-coil 116 is positioned at an appropriate location within the right atrium chamber 120 of the heart 101 or a major vein, such as the superior vena cava, leading to the right atrium chamber 120 of the heart 101.

Additional configurations of sensing, pacing and defibrillation electrodes can be included in the intracardiac lead system to allow for various sensing, pacing, and defibrillation capabilities of multiple heart chambers. In one configuration, the intracardiac lead system may include only a single lead with electrodes positioned in the right atrium or the right ventricle. In another configuration, the intracardiac lead system may include the right atrial and ventricular leads shown in FIG. 1, in addition to one or more leads having electrodes positioned to sense cardiac activity and provide stimulation pulses to the left atrium and/or the left ventricle. Such configurations allow for various sensing, pacing, and defibrillation capabilities, such as, for example, bi-ventricular or bi-atrial sensing, pacing or cardioversion/defibrillation.

In one configuration, the intracardiac lead system 102 may include endocardial sensing, pacing or cardioversion/defibrillation leads (not shown) that are advanced into the coronary sinus and coronary veins to locate the distal electrode(s) adjacent to the left ventricle or the left atrium. The distal end of such coronary sinus leads is advanced through the superior vena cava, the right atrium 120, the valve of the coronary sinus, the coronary sinus, and into a coronary vein communicating with the coronary sinus, such as the great vein. The ICD may also include a can electrode 209. Other intracardiac lead and electrode arrangements and configurations known in the art are also possible and considered to be within the scope of the present system.

The ventricular and atrial lead systems 104, 106 include conductors for communicating sense, pacing, and defibrillation signals between the cardiac defibrillator 100 and the electrodes and coils of the lead systems 104, 106. As is shown in FIG. 1, ventricular lead system 104 includes a conductor 108 for transmitting sense and pacing signals between the RV-tip electrode 112 and an RV-tip terminal 202 within the ICD 100. A conductor 110 of the ventricular lead system 104 transmits sense signals between the RV-coil or ring electrode 114 and an RV-coil terminal 204 within the ICD 100. The ventricular lead system 104 also includes conductor 122 for transmitting sense and defibrillation signals between terminal 206 of the ICD 100 and the SVC-coil 116. The atrial lead system 106 includes conductors 132, 134 for transmitting sense and pacing signals between terminals 212, 210 of the cardiac defibrillator 100 and A-tip and A-ring electrodes 152 and 154, respectively.

Figure 2:
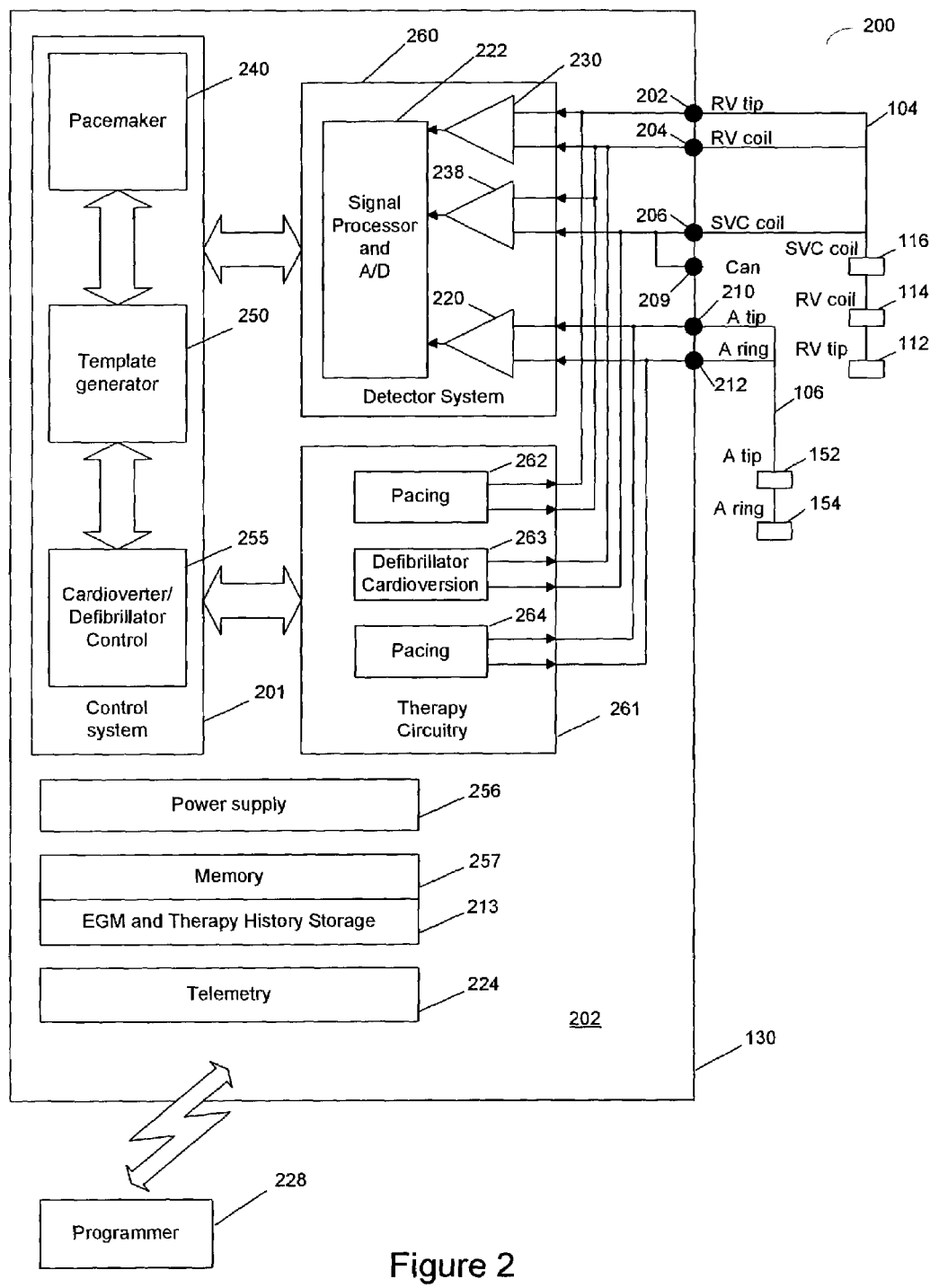
FIG. 2 is a block diagram of an implantable cardioverter/defibrillator with which supraventricular rhythm characterization of the present invention may be implemented.

Referring now to FIG. 2, there is shown a block diagram of an embodiment of a cardiac rhythm management system configured as an ICD 200 suitable for implementing an SVR characterization methodology of the present invention. FIG. 2 shows the ICD 200 divided into functional blocks. It is understood by those skilled in the art that there exist many possible configurations in which these functional blocks can be arranged and implemented. The example depicted in FIG. 2 is one possible functional arrangement. The ICD 200 includes cardiac rhythm management circuitry 202 for receiving cardiac signals from a heart (not shown in FIG. 2) and delivering electrical energy in the form of pacing, cardioversion or defibrillation pulses to the heart. The ICD 200 includes an intracardiac lead system with right ventricular lead 104, and right atrial lead 106 as previously discussed.

In one embodiment, the cardiac rhythm management circuitry 202 is encased and hermetically sealed in a housing 130 suitable for implanting in a human body as is known in the art. Power to the ICD 200 is supplied by an electrochemical battery power supply 256 housed within the ICD 200. A connector block (not shown) is additionally attached to the ICD housing 130 to allow for the physical and electrical attachment of the intracardiac lead system conductors to the cardiac rhythm management system circuitry 202.

The cardiac rhythm management circuitry 202 may be configured as a programmable microprocessor-based system, with a control system 201 and a memory circuit 257. The memory circuit 257 stores parameters for various pacing, defibrillation, and sensing modes. The memory circuit 257 may also store data indicative of cardiac signals received by other components of the cardiac rhythm management circuitry 202. The control system 201 and memory circuit 257 cooperate with other components of the cardiac rhythm management circuitry 202 to perform operations involving the characterization of a patient's supraventricular rhythm according to the principles of the present invention, in addition to other sensing, pacing, and defibrillation functions. Data storage 213 may also be provided to store historical EGM and therapy data. Such data may be transmitted to an external programmer unit 228 and used for various diagnostic purposes and as needed or desired.

Telemetry circuitry 224 is coupled to the cardiac rhythm management circuitry 202 to allow the ICD 200 to communicate with an external programmer unit 228. In one embodiment, the telemetry circuitry 224 and the programmer unit 228 use a wire loop antenna and a radio frequency telemetric link to receive and transmit signals and data between the programmer unit 228 and telemetry circuitry 224. In this manner, programming commands and data are transferred between the cardiac rhythm management circuitry 202 and the programmer unit 228 during and after implant. The programming commands allow a physician to set or modify various parameters used by the ICD. These parameters may include setting pacing modes, pacing intervals, lower rate pacing limits, or setting an independent lower rate limit for use during SVR characterization, for example. In addition, the cardiac rhythm management system 200 may download to the programmer unit 228 stored cardiac data pertaining to sensed arrhythmic episodes within the heart, SVR characterization information, and subsequent therapy or therapies applied to correct the sensed arrhythmic event.

Cardiac signals sensed through use of the defibrillation coils or electrodes 114, 116 are far-field signals, also referred to as morphology or shock channel signals, as are known in the art. More particularly, the right ventricle shock channel signal may be detected as a voltage developed between the RV-coil 114 and the SVC-coil 116. A shock channel signal may also be detected as a voltage developed between the RV-coil 114 and SVC-coil 116 in combination with the can electrode 209. Right ventricle shock channel signals are sensed and amplified by a right ventricle shock EGM amplifier 238 located in the detector system 260. The output of the right ventricle EGM amplifier 238 is coupled to the signal processor and A/D converter 222 in the detector system 260. The signal processor and A/D converter 222 converts the signals from analog to digital form and communicates the signals to the control system 201.

Cardiac signals sensed through use of the RV-tip electrode 112 are near-field signals or rate channel signals as are known in the art. The right ventricle rate channel signal may be detected as a voltage developed between the RV-tip electrode 112 and the RV-coil 114. In the embodiment of the ICD 200 depicted in FIG. 2, RV-tip and RV-coil electrodes 112, 114 are shown coupled to a V-sense amplifier 230 located within the detector system 260. Right ventricle rate channel signals received by the V-sense amplifier 230 are communicated to the signal processor and A/D converter 222. The signal processor and A/D converter 222 converts the signals from analog to digital form and communicates the signals to the control system 201.

A-tip and A-ring electrodes 152, 154 are shown coupled to an A-sense amplifier 220 located within the detector system 260. Atrial signals received by the A-sense amplifier 220 in the detector system 260 are communicated to the signal processor and A/D converter 222. The A-sense amplifier serves to sense and amplify the A-wave signals. The signal processor and A/D converter 222 converts the sensed signals from analog to digital form and communicates the signals to the control system 201.

The pacemaker 240 located within the control system 201 communicates pacing signals to the RV-tip and A-tip electrodes 112 and 152, respectively, according to a preestablished pacing regimen under appropriate conditions. Control signals, developed in accordance with a pacing regimen, are initiated in the pacemaker 240 and transmitted to the therapy circuitry 261 where pacing pulses are generated. In one example, pacing pulses may be provided to the right ventricle by the right ventricle pacing circuit 262, and/or to the right atrium by the right atrial pacing circuit 264. A pacing regimen may be modified by the control system to facilitate the SVR characterization in accordance with the invention.

Cardioversion/defibrillation control signals may be developed in the cardioverter/defibrillation control system 255 to initiate a high energy pulse. High energy cardioversion/defibrillation pulses are generated by the defibrillator/cardioversion circuitry 263 in response to detection of fibrillation or tachycardia. The high energy cardioversion/ defibrillation pulses may be directed through the leads to the right ventricle, for example, to terminate ventricular tachycardia or ventricular fibrillation if required.

The ICD 200 depicted in FIG. 2 is well-suited for implementing SVR characterization according to the principles of the present invention. In the embodiment shown in FIG. 2, the SVR characterization processes of the present invention are largely controlled by template generator 250. The shock channel and rate channel signals are sensed by appropriate electrodes and amplified by the EGM 238 and V-sense 230 amplifiers as described above. These signals are transferred through the A/D converter 222 and may be stored for later processing. It is understood that the required shock and rate channel signals may be developed and processed by components other than those depicted in FIG. 2 for system architectures that differ from the system architectures described herein.

Characterization of supraventricular rhythm may be attempted periodically by attempting to acquire a sufficient number of SVR-representative beats during one session to characterize the patient's normally conducted supraventricular rhythm. The SVR characterization session may be attempted, for example, during a period of time that intrinsic beats spontaneously emerge, or emerge after modification of pacing parameters. However, if the heart is being intermittently or consistently paced, SVR characterization during the SVR characterization session may fail due to a lack of a sufficient number of intrinsic beats. If previous attempts to characterize the patient's supraventricular rhythm fail, collection of SVR-representative beats during a number of intervals, some of which are noncontiguous may be implemented. After a sufficient number of SVR-representative beats have been collected during the plurality of intervals, the patient's supraventricular rhythm may be characterized using the collected beats.

In accordance with an embodiment of the invention, cardiac beats suitable for SVR characterization are collected during a plurality of intervals, some of which are noncontiguous. Pacing parameters may be modified during the plurality of intervals to encourage the development of intrinsic beats. If one or more cardiac beats suitable for SVR characterization are detected during the intervals, the beat waveforms or beat waveform features may be stored. When a sufficient number of cardiac beat waveforms or beat waveform features are collected, for example, 16 beats, the beats may be processed to characterize the patient's supraventricular rhythm. Alternatively, the cardiac beats may be processed on a beat-by-beat basis until a sufficient number of beats have been processed to determine the patient's supraventricular rhythm.

A cardiac beat suitable for SVR characterization in accordance with the principles of the invention, is representative of a normally conducted beat wherein electrical impulses derive in the atria and are conducted to the ventricles producing an atrial-paced rhythm. An SVR-representative beat may include beats produced, for example, by a normal sinus rhythm or atrial tachyarrhythmia. An SVR-representative beat may not include a beat originating in the ventricles, including ventricular tachyarrhythmias and premature ventricular contractions. Other criteria may also be defined to further qualify a beat for SVR characterization.

According to one embodiment of the invention, one or more criteria may be established to classify an SVR-representative beat. Qualified beats used for SVR characterization in accordance with this embodiment are normally conducted beats as described above. Four additional criteria may be used to further classify a cardiac beat as suitable for SVR characterization. First, the beat and the preceding beat must be intrinsic beats. Second, the preceding V-V interval must be larger than approximately 500 ms and must be regular. A beat is classified as a "regular" beat when the RR interval is larger than 87.5% and less than 150% of the average RR interval. An RR interval is measured as an interval between Vs to Vs, Vs to Vp, Vp to Vs, or Vp to Vp events, where Vs is the ventricular sensed event detection time and Vp is the ventricular pace pulse delivery time. The initial RR average (RRavg) may be calculated as the average of the first four RR intervals. The RRavg may be calculated as a running average. The V-V interval is the interval between successive ventricular beats. Third, the shock channel R-wave amplitude must be larger than approximately 25% of the maximum value of the A/D converter and must not be saturated. Finally, the rate channel R-wave must be larger than approximately 50% of the maximum value of the A/D converter and must not be saturated for more than one consecutive sample. If all of these conditions are detected, then the beat is considered a qualified beat suitable for characterizing the patient's supraventricular rhythm.

Figure 3:
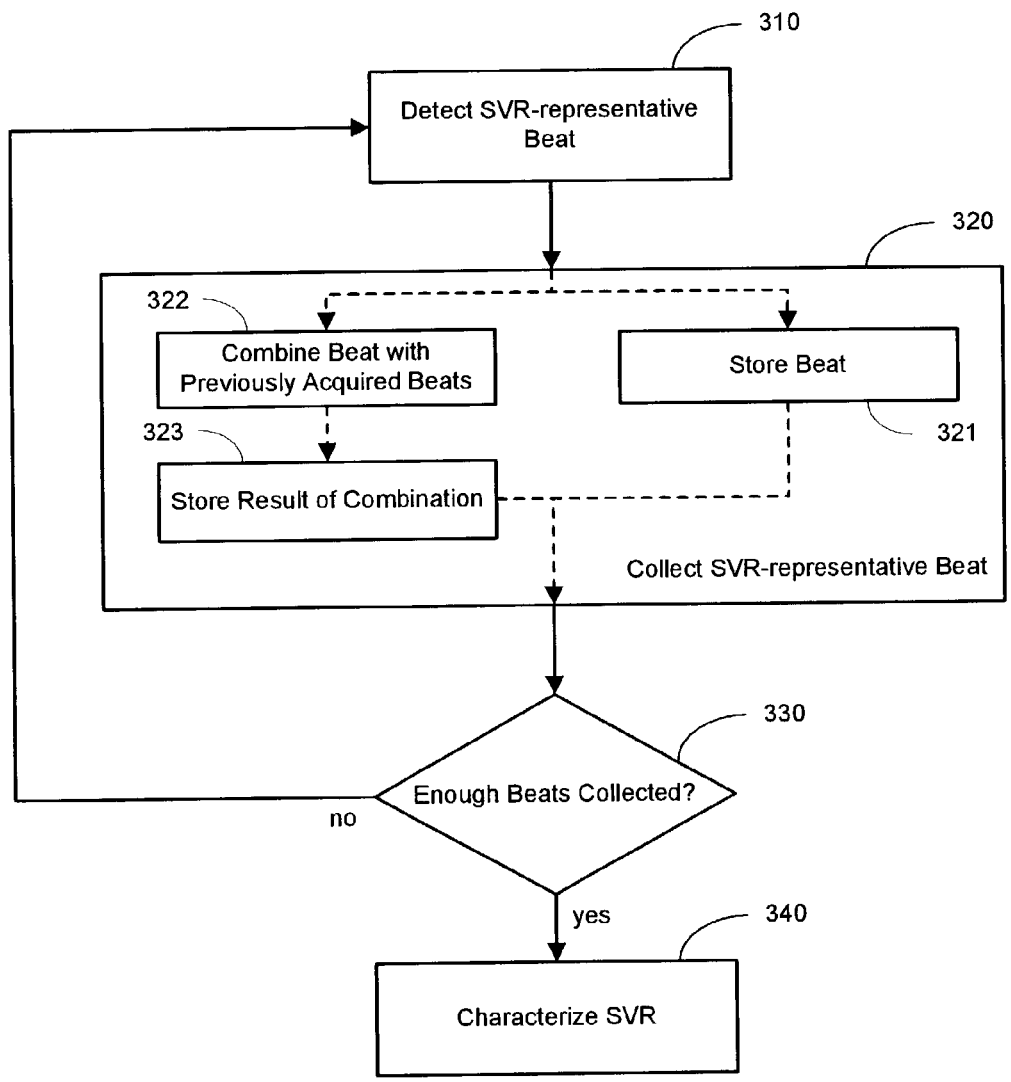
FIG. 3 is a flowchart of a method for characterizing supraventricular rhythm by collecting cardiac beats in accordance with an embodiment of the present invention.

FIG. 3 is a flowchart illustrating a method for characterizing a patient's supraventricular rhythm in accordance with an embodiment of the invention. Cardiac beats representative of a patient's supraventricular rhythm are detected 310. SVR-representative beats are collected 320 during a plurality of periods, some of which are noncontiguous. In one example, an SVR-representative beat may be collected 320 by storing 321 the waveform of the SVR-representative beat. In another example, the SVR-representative beat may be collected 320 by combining 322 the beat with previously acquired SVR-representative beats and storing 323 the result of the combination.

If enough SVR-representative beats have not been collected 330, additional SVR-representative beats may be detected and collected 310 during subsequent time periods. If enough SVR-representative beats have been collected 330, the patient's supraventricular rhythm is characterized 340.

If a patient's heart is paced intermittently, a sufficient number of SVR-representative beats may be collected for SVR characterization as described above without modification of pacing parameters. However, the pacing regimen of some patients does not allow the development of intrinsic beats. For these patients, it may be necessary to modify one or more pacing parameters to elicit intrinsic beats suitable for SVR characterization.

Figure 4:
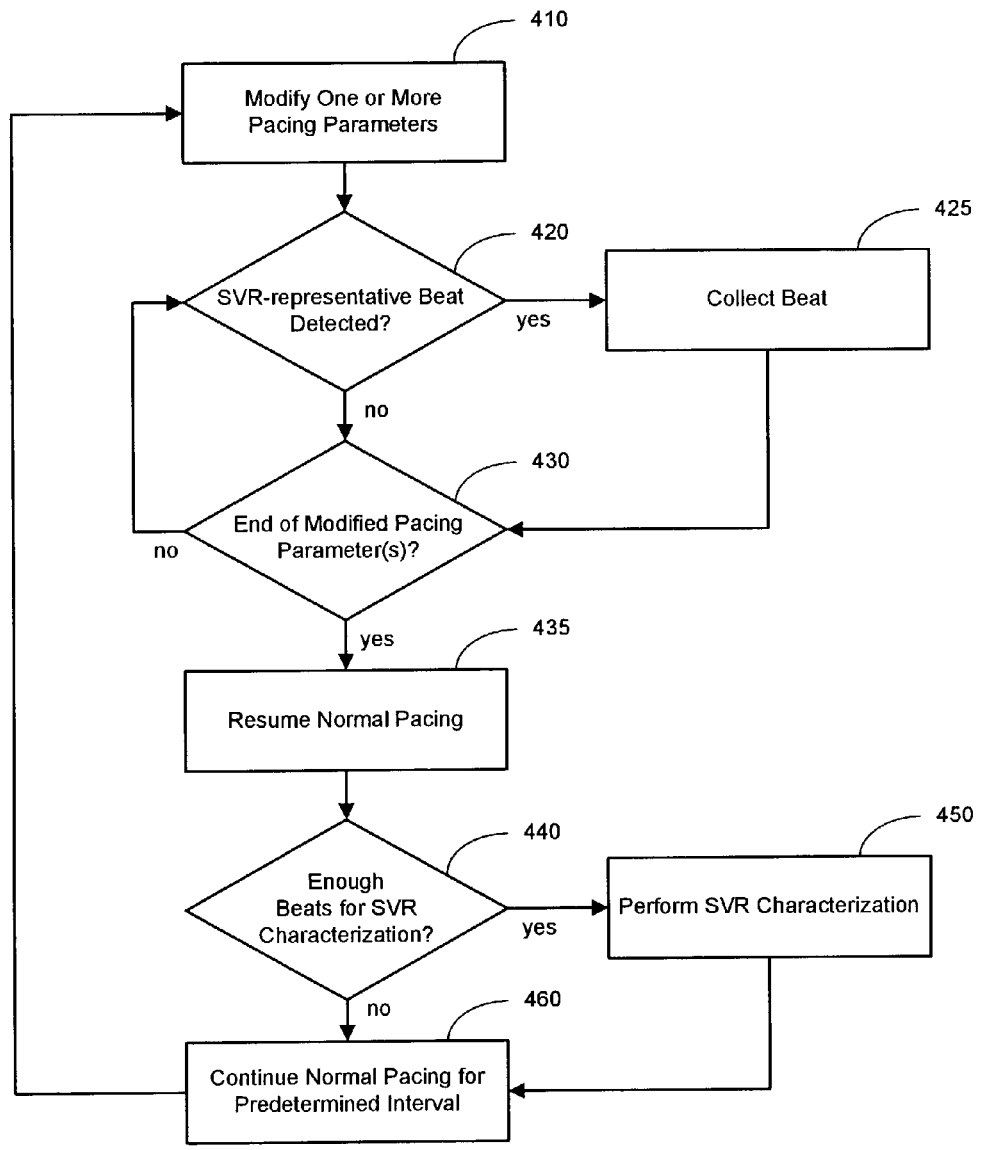
FIG. 4 is a flowchart of a method for characterizing supraventricular rhythm during one or more periods having modified pacing parameters in accordance with an embodiment of the invention.

FIG. 4 is a flowchart illustrating a method for characterizing a patient's supraventricular rhythm according to principles of the present invention. According to an embodiment of the invention, prior to SVR characterization, the patient's heart is being intermittently or consistently paced with pacing pulses developed by the ICD and applied to one or more of the heart chambers through the lead system as described above. Periodically, one or more pacing parameters are modified 410 to allow the spontaneous development of one or more intrinsic beats. The one or more pacing parameters that may be modified include tracking and rate responsiveness, and/or one or more pacing rate or timing intervals, for example. The pacing parameters may be modified abruptly, or gradually within a particular time interval, or incrementally each beat. Modification of the one or more pacing parameters may allow the development of intrinsic beats.

Patient conditions may be monitored during the time pacing parameters are modified. The period of pacing parameter modification may be terminated and normal pacing reestablished if any of a predetermined set of patient conditions are detected. For example, patient conditions that terminate the pacing parameter modification may include 1) the patient's physiologic heart rate demand increases beyond an acceptable limit, 2) a predetermined number of beats with modified pacing parameters is exceeded, 3) the patient's average heart rate becomes elevated, or 4) a predetermined number of paced beats are detected after pacing parameters are modified.

Following detection of intrinsic beats, a predetermined number of beats, for example, four beats, may be required to allow for morphology stabilization before beats are collected. After morphology stabilization, if the intrinsic beats are SVR-representative beats 420 suitable for SVR characterization they are collected 425. In one example, the cardiac beats are collected by storing the beat waveforms. In another example, the cardiac beats are collected by combining each beat with previously collected beats and storing the result of the combination. SVR-representative beats may be collected until the interval of modified pacing parameters ends 430 and normal pacing is resumed 435. When enough SVR-representative beats have been collected 440, SVR characterization is performed 450. Normal pacing may be continued for a predetermined interval 460. The process described in steps 410–460 may be repeated until a sufficient number of cardiac beats for SVR characterization have been collected.

Figure 5:
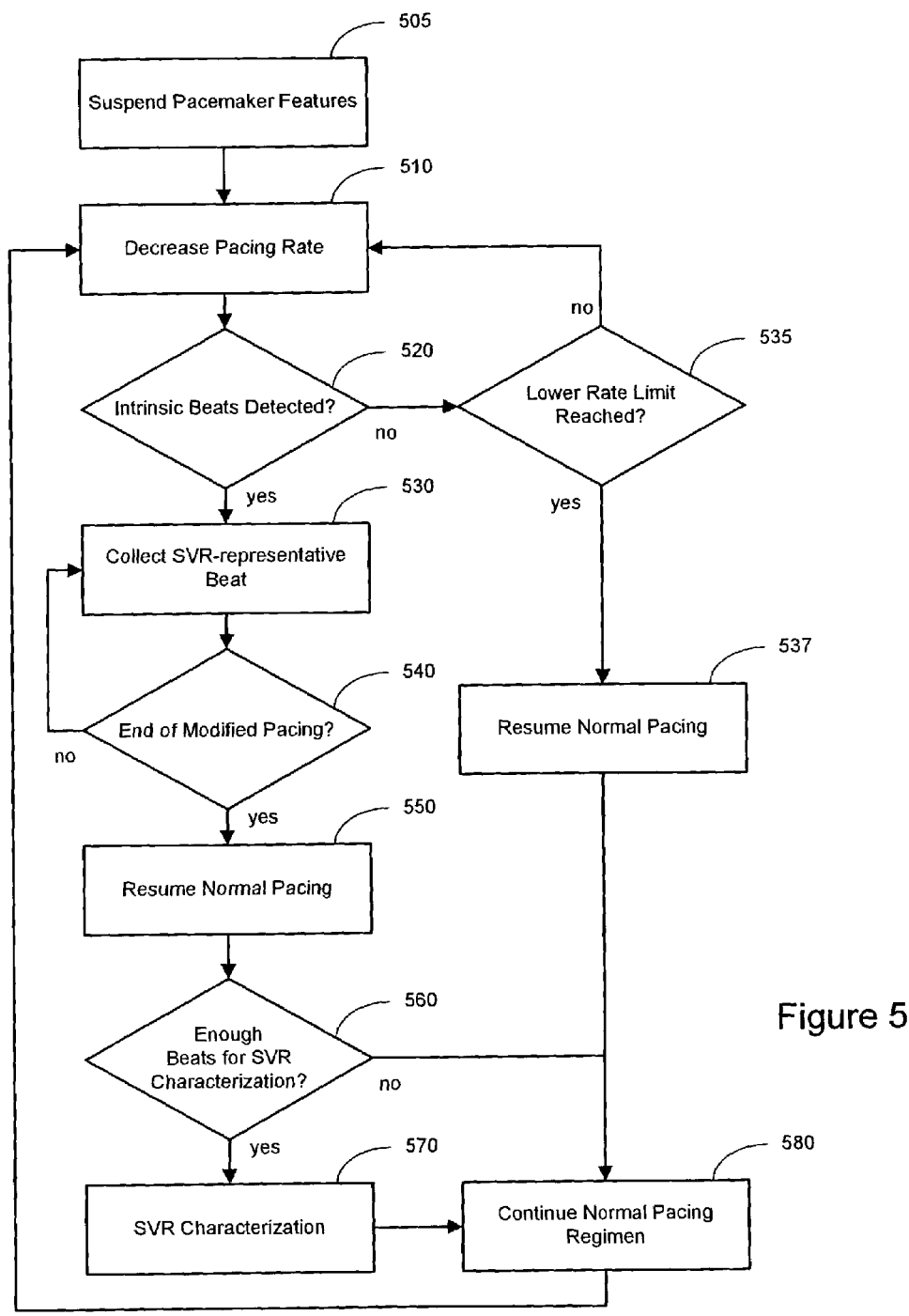
FIG. 5 is a flowchart of a method for characterizing supraventricular rhythm using SVR-representative beats collected during periods having a decreased pacing rate in accordance with an embodiment of the present invention.

In one exemplary embodiment, illustrated in the flowchart of FIG. 5, beats are collected for SVR characterization during a number of periods having a decreased pacing rate. The periods of decreased pacing rate may occur, for example, during a search hysteresis session having an increased pacing escape interval to encourage the development of a spontaneous cardiac rhythm.

Prior to decreasing the pacing rate, patient conditions may be checked to ensure patient conditions indicate that pacing parameters may be modified. An exemplary set of patient conditions that typically must be present for pacing parameter modification to proceed include the following conditions: 1) rate response sensors indicate low patient physiologic heart rate demand, 2) time of day window indicates usual time for low patient activity, e.g., 1 a.m. to 4 a.m., 3) V rate is very low, e.g., in the lowest quartile of rates detected over the past 24 hours, and 4) SVR characterization has not been performed for more than a predetermined period, such as 24 hours, or other time period.

If conditions indicate that pacing parameters may be modified, the pacemaker features that may interfere with collection of beats for SVR characterization may be suspended 505. An exemplary set of features that may be suspended include, for example, 1) dynamic AV delay, 2) dynamic post ventricular refractory period (PVARP), 3) AV search hysteresis, 4) rate hysteresis offset, 5) sensed AV delay offset, 6) PVARP after premature ventricular contraction (PVC), 7) dynamic ventricular refractory period (VRP), and 8) ventricular rate regularization (VRR).

Pacing parameters may be modified by incrementally increasing a pacing interval 510 by a predetermined amount each beat until a lower rate limit is reached 535. In one embodiment, the Vp-Vp interval is incrementally increased by approximately 100 ms each beat until a lower rate limit, such as about 45 bpm is reached. Lengthening the Vp-Vp interval may allow intrinsic beats to emerge. If intrinsic beats are detected 520 while the Vp-Vp interval is increased, SVR-representative beats may be processed, stored for later processing or otherwise collected 530. If intrinsic beats do not develop 520 after the lower rate limit is reached 535, then normal pacing is resumed 537.

After the pacing interval has been increased for a predetermined period 540 the normal pacing regimen may be resumed 550. If a sufficient number of SVR-representative beats have been collected 560 during the period of modified pacing, SVR characterization may be performed 570. If a sufficient number of SVR-representative beats have not been collected 560, then the normal pacing regimen may be continued 580 for a period of time. Additional attempts to collect SVR-representative beats may be made periodically according to the processes described at blocks 505–540 until a sufficient number of beats have been collected.

Figure 6:
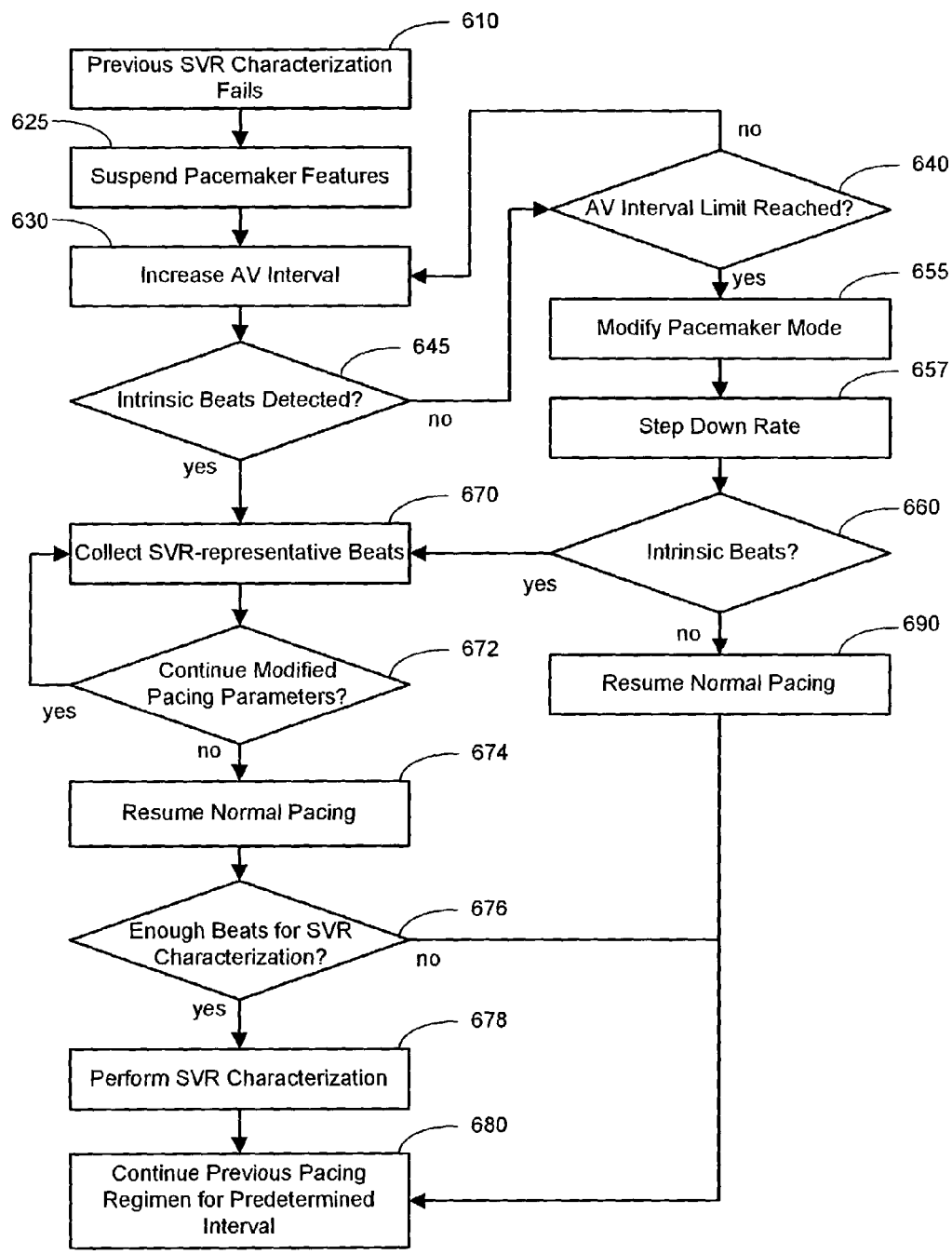
FIG. 6 is a flowchart of a method for characterizing supraventricular rhythm using SVR-representative beats collected during periods having an increased AV interval in accordance with an embodiment of the present invention.

Turning now to the flowchart of FIG. 6, various processes are illustrated for characterization of a patient's supraventricular rhythm according to another embodiment of the present invention. In this exemplary embodiment, a dual chamber device capable of pacing and sensing both the right atrium and the right ventricle senses and paces the heart.

According to a method of the present invention depicted in FIG. 6, if previously attempted methods of SVR characterization fail 610, collection of SVR-representative beats may be attempted during a number of noncontiguous time periods. SVR-representative beats detected during the time periods may be collected and used for SVR characterization.

Pacemaker features that may interfere with the spontaneous emergence of intrinsic beats during pacing parameter modification are suspended 625. An exemplary set of pacemaker features that may be suspended during pacing parameter modification include, for example: 1) dynamic AV delay, 2) dynamic post ventricular refractory period (PVARP), 3) AV search hysteresis, 4) rate hysteresis offset, 5) sensed AV delay offset, 6) PVARP after premature ventricular contraction (PVC), 7) dynamic ventricular refractory period (VRP), and 8) ventricular rate regularization (VRR).

In this example embodiment, the AV interval is increased 630 a predetermined amount each beat until an AV interval limit is reached 640. In one embodiment, the AV interval is increased by approximately 25 ms each beat until the AV interval reaches a limit of approximately 400 ms. If intrinsic beats develop 645 during the time the AV interval is modified, SVR-representative beats may be processed and stored or otherwise collected 670. SVR-representative beats may continue to be collected 670 until the period of increased AV interval ends 672. In one example, the AV interval may be increased for a programmable number of beats, for example 12 to 16 beats.

If intrinsic beats do not develop 645 after increasing the AV interval to the AV interval limit 640, the pacing mode may be modified 655. For example, the pacing mode may be modified from a dual chamber pacing mode to a single chamber pacing mode, or to a non-tracking, non-rate responsive mode. The pacing rate may be stepped down 657 incrementally to a lower rate limit (LRL) to elicit intrinsic beats. If intrinsic beats develop 660 during the time the pacing rate is modified, SVR-representative beats may be processed and stored or otherwise collected 670. If intrinsic beats do not develop 660 during the time the pacing rate is modified, normal pacing is resumed 690. Additional attempts to acquire SVR-representative beats may be repeated at a later time.

After the period of pacing modification ends 672, normal pacing is resumed 674. If enough SVR-representative beats have been collected 676 for SVR characterization, then SVR characterization is performed 678. If a sufficient number of SVR-representative beats have not been collected 676, the normal pacing regimen may be continued 680 for a predetermined time. A period of pacing parameter modification may be periodically initiated following a programmable number of cardiac beats paced according to the normal regimen, for example, 32 to 1024 beats. After the predetermined time has elapsed, collection of additional SVR-representative beats may be attempted by the processes illustrated at blocks 610–670. The processes of blocks 610–670 may be repeated as needed to collect additional SVR-representative beats until enough SVR-representative beats are collected for SVR characterization.

Pacing modification and attempts to acquire SVR-representative beats may be terminated prior to completion if predetermined patient conditions are detected. If pacing modification is terminated, the previous pacing regimen is resumed.

Figure 7:
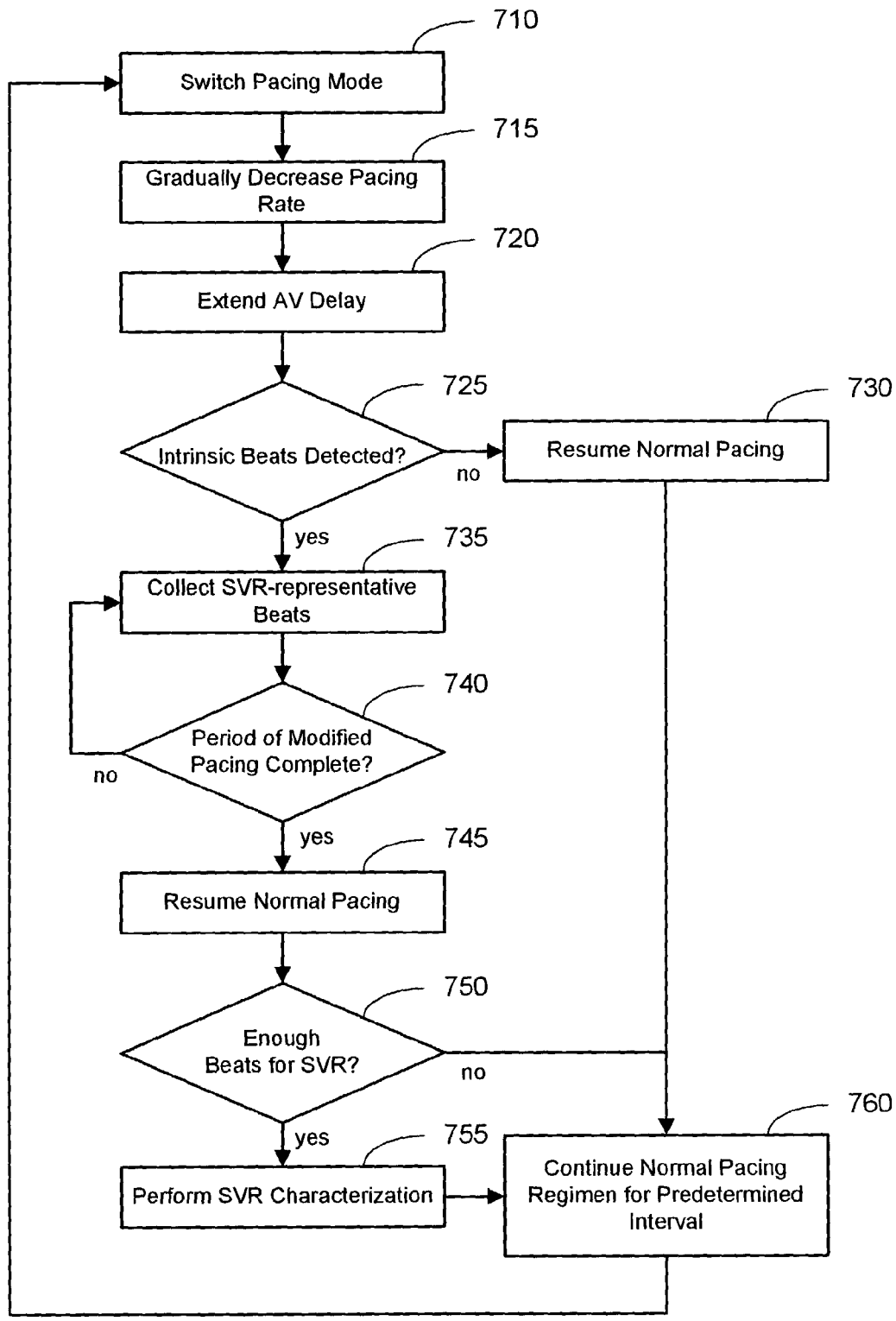
FIG. 7 is a flowchart of a method for characterizing supraventricular rhythm in a dual chamber device in accordance with an embodiment of the present invention.

The flowchart of FIG. 7 illustrates a process for collecting SVR-representative beats and characterizing supraventricular rhythm in a dual chamber device according to an embodiment of the invention. According to this process, the pacing mode is switched 710 to a non-tracking, non-rate responsive mode. For example, if the normal pacing mode is DDD(R), tracking and rate responsiveness are suspended, and the pacing mode is modified to DDI. By this method, the normal pacing mode is modified, and any atrial tachycardia response (ATR) pacing modes are ignored during the period of modified pacing.

Following the pacing mode changes, the pacing rate is gradually slowed 715 to a lower rate limit and the AV delay is abruptly extended 720. The pacing rate may be gradually slowed 715 using an ATR algorithm, for example. The lower rate limit achieved by the gradual decrease in pacing rate 715 may be programmable with a default for tracking the normal programmed lower rate limit.

The AV delay may be increased as much as possible while still maintaining safe tachycardia sensing, such as by up to approximately 400 ms. A safe AV interval for tachycardia sensing is the longest AV interval that prevents ventricular undersensing. An extended AV interval, greater than 350 ms, for example, may create a scenario for possible ventricular undersensing because the ventricular blanking interval following atrial pacing is pushed into the tachycardia rate zone. The following rule may be used for determining the safe AV interval: Longest Safe AV interval=LRI (lower rate interval)−VTI (slowest VT interval)−20 ms (safety window). For example, if the lowest tachycardia zone is 120 bpm, the LRL is 50 bpm, the Longest Safe AV interval=1200 ms−500 ms−20 ms=680 ms.

If no intrinsic beats are detected 725 following the pacing rate and AV delay changes, normal pacing is resumed 730. However, if the pacing modifications elicit intrinsic beats 725, SVR-representative beats are processed, stored or otherwise collected 735 until the period of modified pacing is complete 740.

Following the period of modified pacing 740, normal pacing is resumed 745. Original tracking, rate responsiveness, AV delay and other bradycardia related features may be abruptly resumed. If rate smoothing is programmed on, the pacing rate may be gradually restored, otherwise, the pacing rate may be abruptly restored as in the termination of ATR. Following restoration of the pacing rate, the PVARP may be extended for a single beat if PVARP extension is programmed on to prevent ventricular pacing triggered by erroneous sensing of an atrial signal.

If a sufficient number of SVR-representative beats have been collected 750, SVR characterization is performed 755. Normal pacing may be continued 760 for a period of time. The process described at blocks 710–755 may be repeated periodically until a sufficient number of SVR-representative beats have been collected for SVR characterization.

During the period of pacing modification, various ATR functions may be maintained. For example, ATR up/down counters are maintained during pacing modification. Further, the ATR duration, begin and end markers are emitted responsive to atrial arrhythmia, and ATR episodes are declared and recorded. Restoring ATR after pacing modification results in smoothing the pacing rate down to ATR settings if the ATR lower rate limit is slower than the lower rate limit used for pacing modification. If the ATR lower rate limit is faster than that used during pacing modification, the increase in pacing rate may be abrupt.

Figure 8:
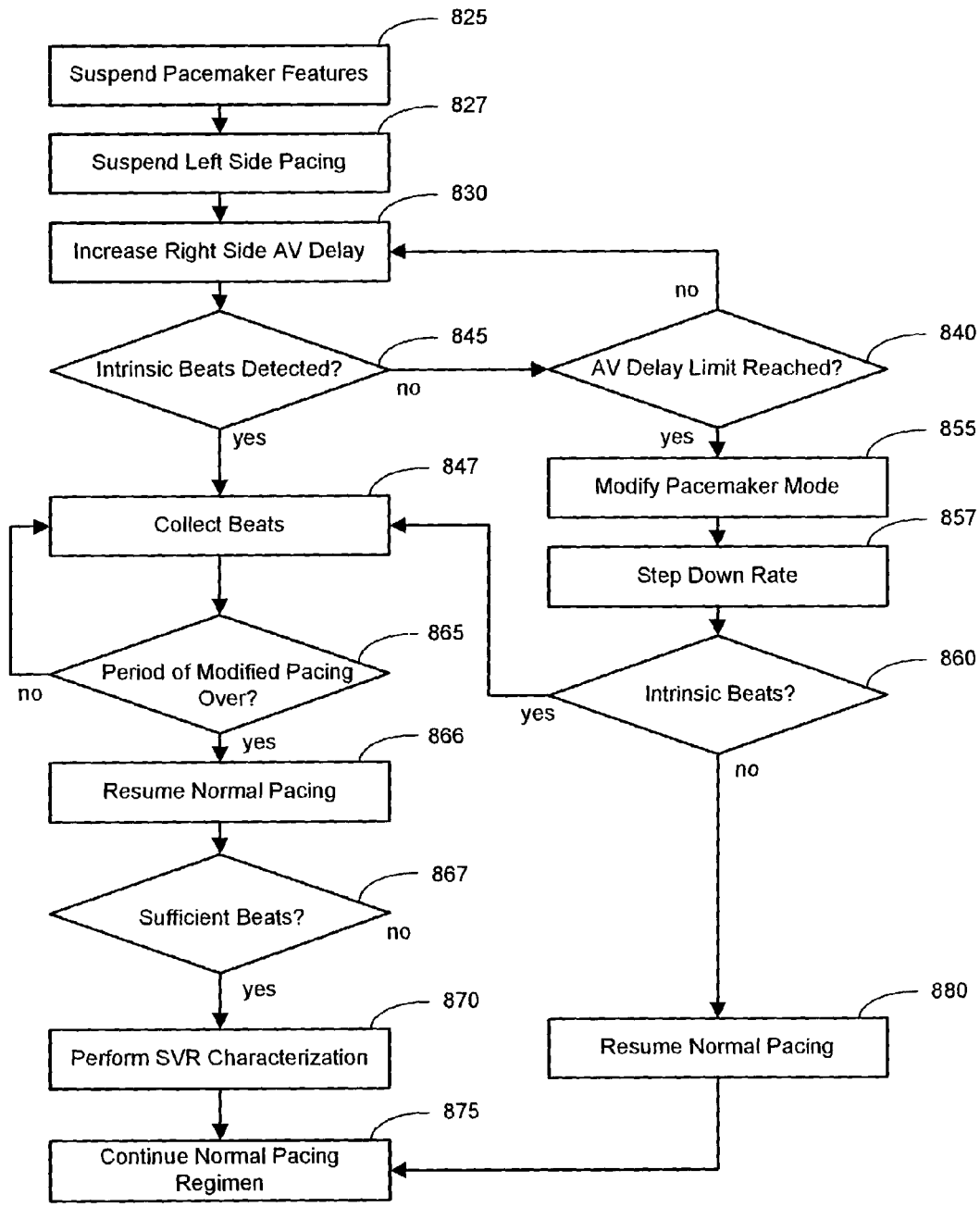
FIG. 8 is a flowchart of a method for characterizing supraventricular rhythm in a bi-ventricular device in accordance with an embodiment of the invention.

Referring to the flowchart of FIG. 8, a process for collecting SVR-representative beats in accordance with an embodiment of the invention is illustrated when a multi-chamber, biventricular device paces the heart, such as a CHF device. The CHF device may be capable of pacing the left and right ventricles and the left and right atria, for example.

During a number of intervals used to collect SVR-representative beats, one or more pacing parameters may be modified to allow the development of intrinsic beats. Pacing modification may be terminated if predetermined patient conditions are detected. In this event, the previous pacing regimen is resumed. Pacemaker features that interfere with collection of SVR-representative beats during pacing modification as previously described above are suspended 825. The left side pacing of the heart may also be suspended 827. Pacing parameters are modified by increasing the right side AV interval 830, by a predetermined amount each beat until an AV interval limit is reached 840. In one embodiment, the AV interval is increased by approximately 25 ms each beat until the AV interval reaches a limit of approximately 400 ms. During the time the AV interval is modified, if intrinsic beats are detected 845, SVR-representative beats may be collected 847 until the period of pacing parameter modification is complete 865.

If no intrinsic beats are detected 845 after increasing the AV delay interval 830 to the AV interval limit 840, the pacing mode may be modified 855. For example, the pacing mode may be modified from a dual chamber pacing mode to a single chamber pacing mode or to a non-tracking, non-rate responsive mode. The pacing rate may be stepped down 857 incrementally to a lower rate limit (LRL) to elicit intrinsic beats. If intrinsic beats are detected 860 while the pacing mode is modified, SVR-representative beats may be collected 847 until the period of pacing parameter modification is complete 865. If no intrinsic beats are detected, the normal pacing regimen is resumed 880.

Following the period of modified pacing 865, if a sufficient number of SVR-representative beats are collected 867, SVR characterization may be performed 870. If a sufficient number of beats are not collected 867, the normal pacing regimen may be continued 875, and periodic attempts to acquire SVR-representative beats may be made in accordance with the process described in blocks 825–867. SVR characterization may be performed after a sufficient number of SVR-representative beats have been collected by these processes.

Other methods of performing SVR characterization while the heart is being paced are described in commonly owned U.S. patent application Ser. No. 10/121,944, filed Apr. 12, 2002 and entitled "Method and System For Characterizing Supraventricular Rhythm During Cardiac Pacing," (GUID.040PA), which is incorporated herein by reference.

Figure 9:
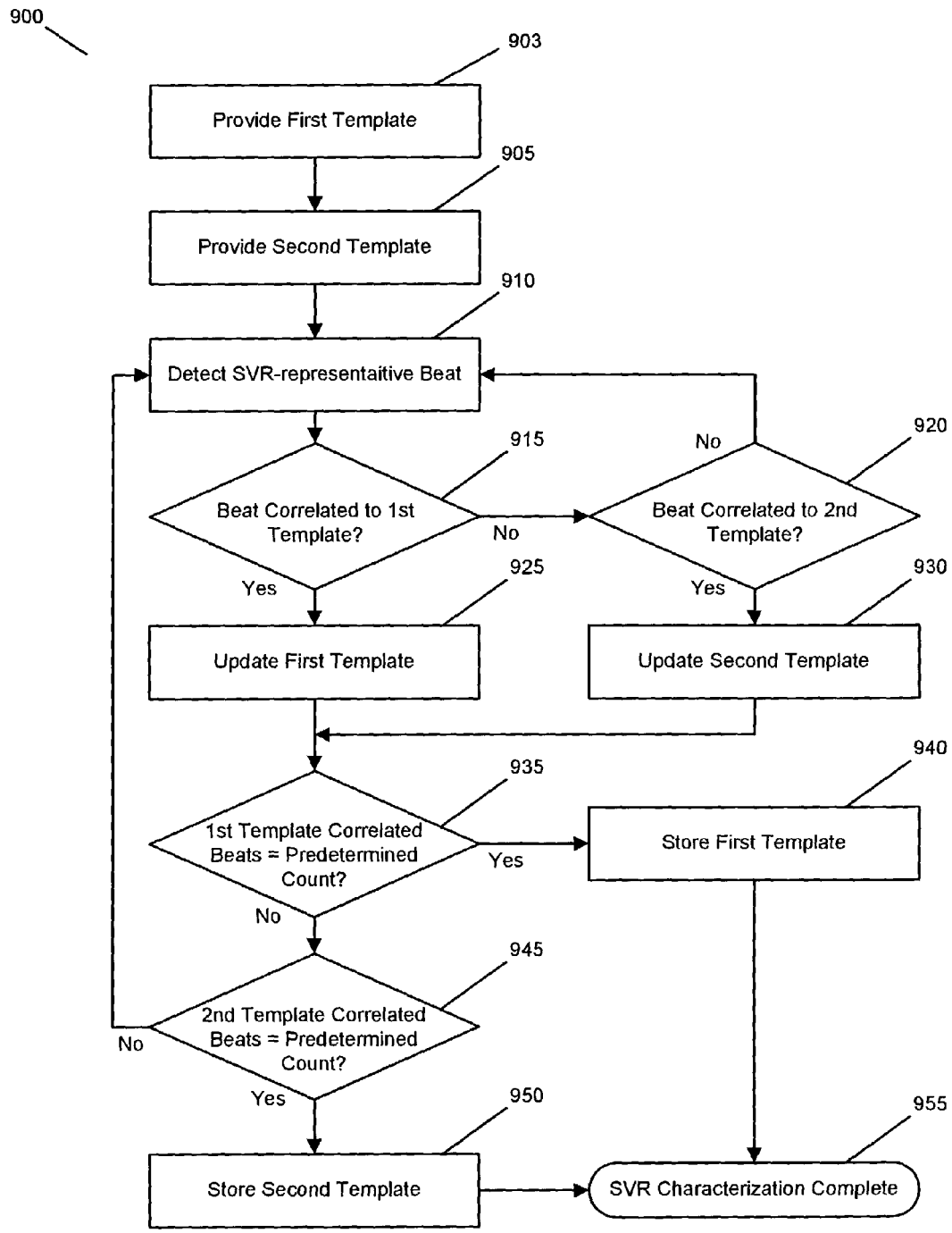
FIG. 9 is a flowchart of a method for characterizing supraventricular rhythm using two templates in accordance with an embodiment of the invention.

The flowchart of FIG. 9 illustrates a method of using multiple templates to quickly acquire a characterization of a patient's supraventricular rhythm in accordance with the present invention. Characterization of supraventricular rhythm may be performed in batch mode after a predetermined number of SVR-representative beat waveforms have been stored. Alternatively, characterization of supraventricular rhythm may be performed on a beat by beat basis as SVR-representative beats are collected.

The template generator provides a first template 903 and a second template 905. The first template can either be retrieved from memory or can be formed from a first SVR-representative beat. The second template can likewise be retrieved from memory, or if it has not previously been stored, it can be formed from the first SVR-representative beat found to be uncorrelated to the first template.

A SVR-representative beat 910 may be used to update the first template 925 if the beat is correlated to the first template 915. If the beat is not correlated to the first template 915, but is correlated to the second template 920, the beat is used to update the second template 930. The following paragraphs describe how correlation of a template and an SVR-representative beat is determined with reference to FIGS. 10–15.

Figure 10:
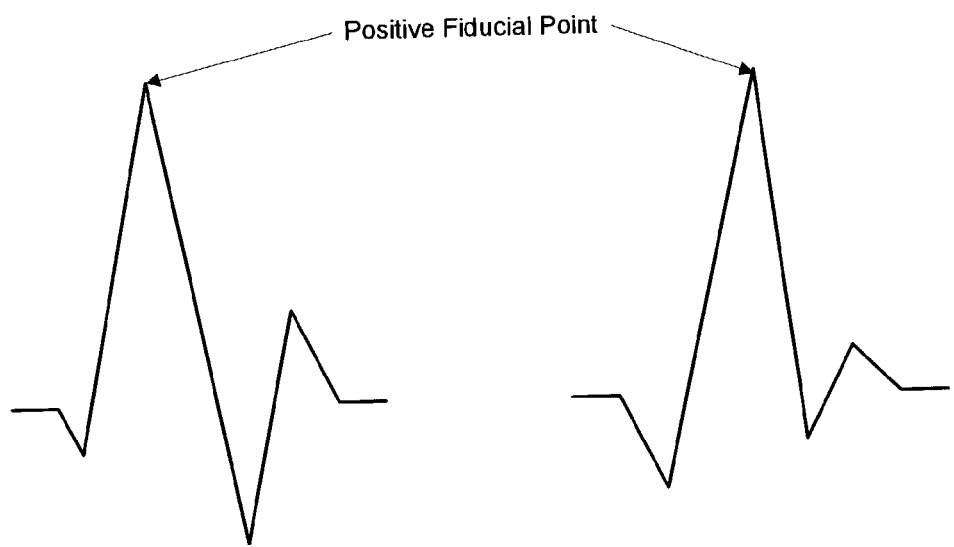
FIGS. 10 and 11 illustrate positive and negative type fiducial points in accordance with an embodiment of the present invention.
Figure 11:
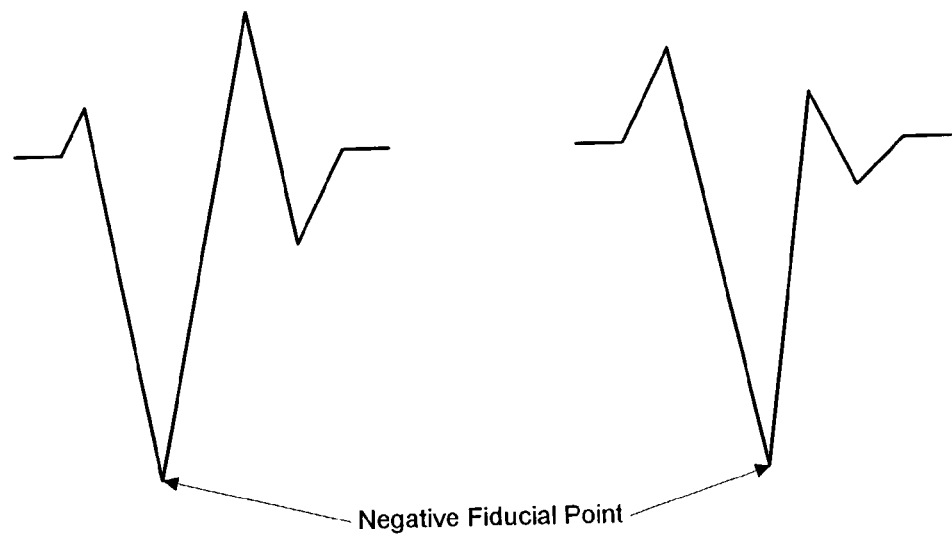

A fiducial point is identified for the template and for the SVR-representative beat. In one embodiment, a fiducial point represents a peak value of the rate channel signal. The fiducial point may be either positive, for a positive peak value, or it may be negative, for a negative peak value. Positive and negative fiducial points are illustrated in FIGS. 10 and 11, respectively.

Following determination of the template fiducial point, a plurality of features of the template are identified as illustrated in FIGS. 12–15. In one embodiment of the invention, five features are initially identified for the shock channel template followed by three additional features determined at midpoints between certain ones of the initial five features.

Feature 3 is selected as the absolute maximum peak in a feature window defined by 31 samples centered at the fiducial point. If the positive peak amplitude is equal to the negative peak amplitude, the positive peak is selected as Feature 3.

Feature 2 is found by searching backward from Feature 3 until a point is reached that meets the following conditions: 1) The search is limited to 10 samples. If no point satisfies the following conditions, then the 10th sample becomes Feature 2; 2) the amplitude is less than 25% of the maximum peak; 3) a turning point is found or the slope is flat, and 4) Feature 2 is at least 4 samples away from Feature 3.

By way of example, let Q(I) represent the current sample. A turning point is found if:

$Q(I-1)Q(I)$ and $Q(I)<Q(I+1)$ for a positive Feature 3

$Q(I-1)Q(I)$ and $Q(I)>Q(I+1)$ for a negative Feature 3    [1]

Figure 12:
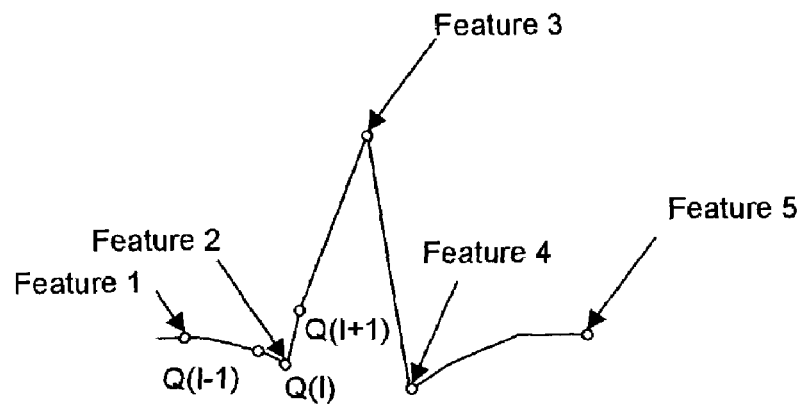
FIGS. 12–15 show morphological features of cardiac signals in accordance with an embodiment of the present invention.

As is shown in FIG. 12, Q(I) is selected as Feature 2. As such, Feature 2 is selected as a turning point.

Figure 13:
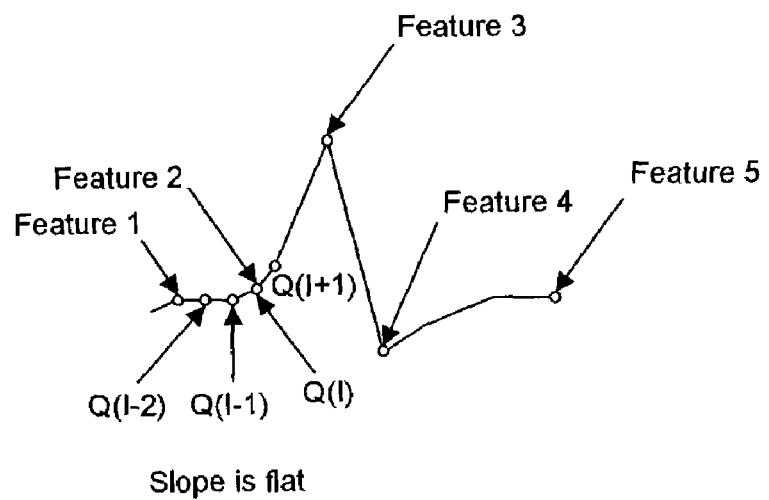

The slope is considered flat, as shown in FIG. 13, if abs(Q(I+1)−Q(I−1))<4 and abs(Q(I+1)−Q(I−2))<4, in the case when the A/D converter maximum value is 128. In the illustrative depiction of FIG. 13, Q(I) is selected as Feature 2. As such, Feature 2 is selected as a flat slope point.

Feature 4 is found by searching forward starting from Feature 3 until a point is reached that meets the following conditions: 1) The search is limited to 16 samples. If no point satisfies the following conditions, then the 16th sample becomes Feature 4; 2) the amplitude is less than 25% of the maximum peak; and 3) a turning point is found or the slope is flat.

By way of example, let Q(I) represent the current sample. A turning point is found if:

$Q(I+1)Q(I)$ and $Q(I)<Q(I-1)$ for a positive Feature 3

$Q(I+1)Q(I)$ and $Q(I)>Q(I-1)$ for a negative Feature 3    [2]

Figure 14:
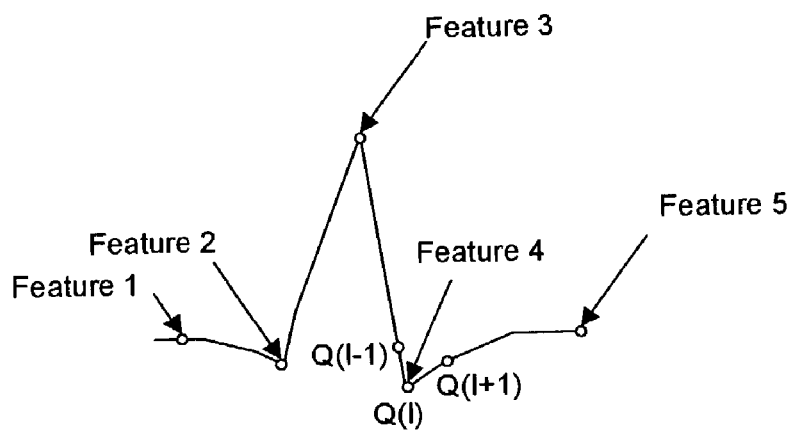

Q(I) is selected as Feature 4, as is shown in FIG. 14.

Figure 15:
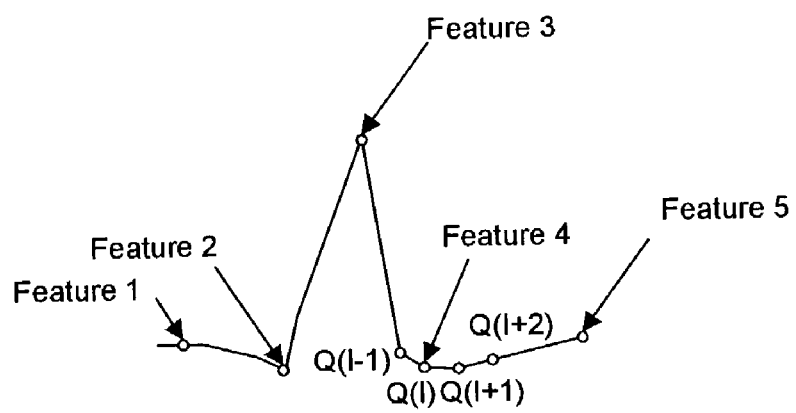

The slope is flat, as shown in FIG. 15, if abs(Q(I−1)−Q(I+1))<4 and abs(Q(I−1)−Q(I+2))<4. In this case, Q(I) is selected as Feature 4.

Feature 1 is selected as the seventeenth sample from the beginning of the detection window. Feature 5 is selected as the last sample of the detection window. Three additional features are selected at the midpoint of Features 1 and 2, the midpoint of Features 2 and 3, and the midpoint of Features 3 and 4, respectively. If a midpoint falls between two sample points, the farthest point in time from Feature 3 is selected. Thus, according to this embodiment, eight feature values (e.g., amplitudes) and their associated locations with respect to the fiducial point and the corresponding fiducial point type are saved for SVR characterization.

The fiducial point of the SVR-representative beat is determined from the rate channel signal of the SVR-representative beat in a manner similar to that set forth above for identifying the template fiducial point. If a positive peak is the template fiducial point, then a positive peak is the fiducial point of the SVR-representative beat. The shock channel waveforms of the template and the SVR-representative beat are aligned using the fiducial points of the template and the SVR-representative beat. The features of the SVR-representative beat are determined at the locations relative to the fiducial point previously determined for the template. The template and the SVR-representative beat are compared by calculating a feature correlation coefficient (FCC). In one particular embodiment, Equation 3, provided below, is used to compute the FCC between the template features and the beat features.

$$FCC = \frac{\left(N\sum_{i=1}^{N} X_i Y_i - \left(\sum_{i=1}^{N} X_i\right)\left(\sum_{i=1}^{N} Y_i\right)\right)^2}{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)} \quad [3]$$

where Xi represents template N features and Yi represents beat N features, and N=8 in this illustrative example. The sign of the numerator term is checked before squaring. If the numerator is negative, the beat is uncorrelated, and the remainder of the computation need not be performed.

If the FCC is greater than or equal to a predetermined value, for example 0.95, then the SVR-representative beat is correlated to the template. If the FCC is less than the predetermined value, then the SVR-representative beat is uncorrelated to the template.

Returning now to FIG. 9, if a beat is correlated to the first template 915, it is used to update the first template 925. If the beat is uncorrelated to the first template 915, but is correlated to the second template 920, the beat is used to update the second template 930. A template is updated by point-by-point addition of the template waveform and the shock channel waveform of the SVR-representative beat after alignment of the waveforms using previously determined fiducial points.

The templates continue to be updated in this manner until either the first or the second template is updated with a predetermined number of beats, for example, 6 beats. If the first template is updated with a predetermined number of beats 935, the first template is stored 940 as the characterization of the patient's supraventricular rhythm and SVR characterization is complete 955. If the first template is not correlated to the predetermined number of beats 935 but the second template has been correlated to the predetermined number of beats 945, the second template is stored 950 as a representative of the patient's supraventricular rhythm and SVR characterization is complete 955.

When a SVR-representative beat is correlated to a template, it represents a template beat and is used to update the template. After temporal alignment using the rate channel fiducial points, the shock channel waveforms of the template and the SVR-representative beat may be combined by point by point addition.

Additional details of a dual template SVR characterization methodology suitable for use within the context of the present invention is disclosed in previously referenced patent application Ser. No. 10/105,875, filed Mar. 25, 2002, and entitled "Method and System for Characterizing a Representative Cardiac Beat Using Multiple Templates," (GUID.041US01).

Figure 16:
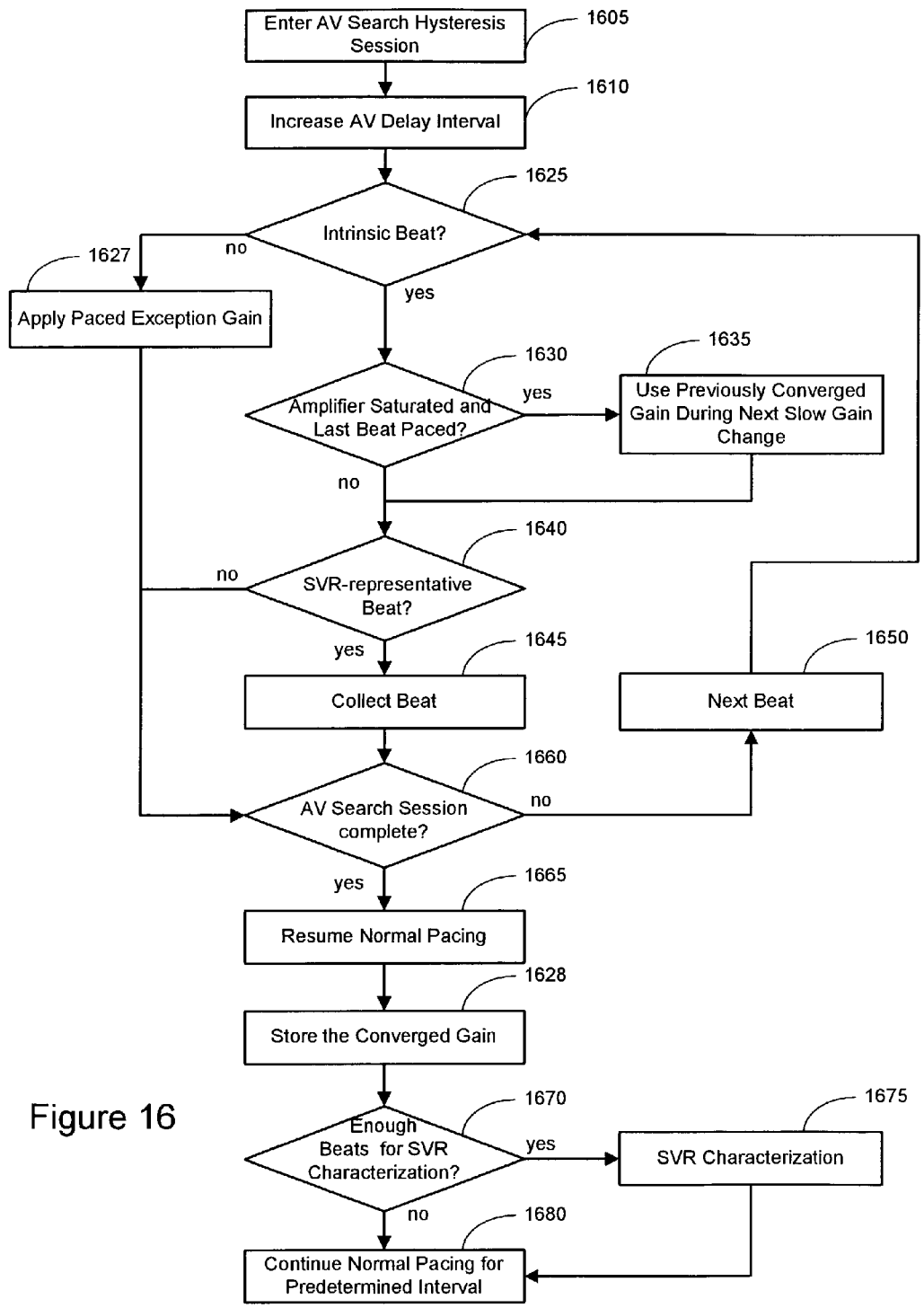
FIG. 16 is a flowchart illustrating a method for characterizing supraventricular rhythm using an automatic gain control in accordance with an embodiment of the invention.

The flowchart of FIG. 16 illustrates an embodiment of the present invention wherein one or more AV search hysteresis sessions are used to detect SVR-representative beats for SVR characterization. The detection of SVR-representative beats may be enhanced with a modified rate channel automatic gain control (AGC) process.

Ventricular paced beats typically trigger a significant increase in the V-sense amplifier gain that often results in saturation of the V-sense amplifier by subsequent intrinsic beats. The increased V-sense amplifier gain following paced beats is provided to ensure detection of ventricular tachyarrhythmias with low rate channel amplitudes during pacing. When a ventricular pacing pulse is delivered, the rate channel gain is set to a fixed gain, denoted the paced exception gain. The paced exception gain is optimized to detect an onset of ventricular fibrillation. The paced exception gain is typically larger than the desired gain for detecting intrinsic beats. A large rate channel gain clips the rate channel signals at the V-sense amplifier, preventing the beat to be used as a SVR-representative beat because the fiducial point cannot be accurately determined.

The gain following a ventricular pacing pulse may be converged to a lower gain within a few beats by using an increasingly smaller gain each beat until the V-sense amplifier is no longer saturated by the rate channel signal. However, during the convergence period, the R-waves of the beats detected may heavily saturate the V-sense amplifier and therefore be unusable as SVR-representative beats for SVR characterization.

It may be advantageous to modify the automatic gain control (AGC) during pacing modification so that intrinsic beats may be captured without saturation of the amplifier. The automatic gain control algorithm used to modify the AGC during pacing modification may delay the increase in gain by a predetermined number of beats following a pacing pulse. In the event that tachyarrhythmia begins during pacing modification, delaying the gain increase may delay therapy for several beats, however, it increases the likelihood of acquiring intrinsic beats for SVR characterization.

According to an embodiment of the invention, the rate channel automatic gain control (AGC) algorithm is modified before pacing modification is attempted so that the ventricular rate channel gain is not modified by a paced beat unless N consecutive pacing pulses have occurred since the last beat, where N=1, 2 or 3.

To prevent a lengthy gain convergence process, the V-sense amplifier gain converged at the end of the previous AV search hysteresis session may be saved and used during a subsequent AV search hysteresis session. Since ventricular tachycardia or fibrillation may begin during the AV search hysteresis session, the converged gain may only be used during an AV search period limited to a predetermined value, for example 400 ms. By this method, the AV search hysteresis session begins with the previously converged gain. If an intrinsic beat does not develop during the first lengthened AV interval, the paced exception gain is used.

If the first intrinsic beat in the AV search hysteresis session saturates the V-sense amplifier, the converged gain is applied at the next slow AGC gain change, wherein the gain is not modified by a paced beat unless N consecutive pacing pulses have occurred since the last beat, where N=1, 2 or 3. This procedure allows subsequent beats to be detected at this gain without amplifier saturation.

FIG. 16 illustrates the process of collecting SVR-representative beats during one or more AV search hysteresis sessions using modified automatic gain control. In this embodiment, the ICD operates in DDD mode wherein both the atrium and ventricle are paced and pacing is inhibited when a spontaneous cardiac response is sensed.

Periodically, the pacemaker initiates an AV search hysteresis session 1605. During the AV search hysteresis session, the AV interval is increased 1610 for a programmable number of beats. If no intrinsic beats are detected 1625, the paced exception gain is used 1627. If an intrinsic beat is detected 1625, and if the beat saturates the amplifier 1630, the gain converged during a previous AV search hysteresis session is used during the next slow AGC gain adjustment 1635.

If the detected beat does not saturate the amplifier 1630 and is an SVR-representative beat 1640, the beat is stored 1645. Additional SVR-representative beats may be detected 1640 and collected 1645 until the AV search hysteresis session is complete 1660 and normal pacing resumes 1665. The converged rate channel gain is stored 1628 for later use.

When a sufficient number of beats 1670 have been collected from one or more AV search hysteresis sessions, SVR characterization is performed 1675. The normal pacing regimen may be continued for a predetermined interval 1680. The AV search hysteresis process discussed in connection with blocks 1605–1660 may be repeated to acquire a sufficient number of SVR-representative beats for SVR characterization.

Characterization of a patient's supraventricular rhythm in accordance with the principles of the present invention provides for several advantages. For example, SVR characterization in accordance with the present invention provides a method for characterizing a patient's supraventricular rhythm while the heart is being consistently or intermittently paced. The SVR-representative beats collected by the methods of the invention may be acquired during periods of time that cardiac beats develop spontaneously. These periods of time may involve modification of pacing parameters to encourage the development of intrinsic beats.

Characterization of supraventricular rhythm by other methods may not be possible because a sufficient number of SVR-representative beats cannot be collected while the heart is intermittently or consistently paced. Using the methods of the invention, SVR-representative beats may be collected during a number of non-contiguous intervals. The beats may be processed immediately using various template generation methods, such as the one described above in connection with FIGS. 9–15. Alternatively or additionally, the beats may be stored for later processing to characterize the patient's supraventricular rhythm.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for characterizing a patient's supraventricular rhythm, comprising:
   collecting cardiac beats representative of the patient's supraventricular rhythm during a plurality of periods, of which some are noncontiguous; and
   generating a morphology template characterizing the patient's supraventricular rhythm using the collected cardiac beats.

2. The method of claim 1, wherein collecting the cardiac beats comprises storing the cardiac beats.

3. The method of claim 1, wherein collecting the cardiac beats comprises combining each cardiac beat with previously collected cardiac beats and storing the result of the combination.

4. The method of claim 3, wherein combining each cardiac beat with previously collected cardiac beats comprises performing point-by-point addition of a cardiac beat waveform to a template waveform.

5. The method of claim 1, wherein collecting the cardiac beats comprises:
   modifying a pacing parameter; and
   collecting the cardiac beats during a time in which the pacing parameter is modified.

6. The method of claim 5, wherein collecting the cardiac beats further comprises returning the pacing parameter to an original value.

7. The method of claim 5, wherein modifying the pacing parameter comprises modifying a pacemaker mode.

8. The method of claim 5, wherein modifying the pacing parameter comprises modifying a pacing rate.

9. The method of claim 5, wherein modifying the pacing parameter comprises modifying a pacing interval.

10. The method of claim 5, wherein modifying the pacing parameter comprises suspending one or more pacemaker functions.

11. The method of claim 5, wherein modifying the pacing parameter comprises increasing a pacing escape interval.

12. The method of claim 5, wherein modifying the pacing parameter comprises increasing an AV interval.

13. The method of claim 5, wherein modifying the pacemaker parameter comprises changing a pacemaker mode from a tracking, rate responsive mode to a non-tracking, non-rate responsive mode.

14. The method of claim 5, wherein collecting the cardiac beats during a time in which the pacing parameter is modified comprises collecting the cardiac beats during periodic sessions in which the pacing parameter is modified.

15. The method of claim 14, wherein the periodic sessions in which the pacing parameter is modified occur every 32 to 1024 beats.

16. The method of claim 5, wherein modifying the pacing parameter comprises modifying the pacing parameter to a pacing parameter limit.

17. The method of claim 5, wherein modifying the pacing parameter comprises:
   increasing an AV interval;
   modifying a pacemaker mode if no intrinsic beats are detected during a period having the increased AV interval; and
   slowing a pacing rate to allow intrinsic beats to develop.

18. The method of claim 5, wherein modifying the pacing parameter comprises switching a pacemaker mode from a dual chamber mode to a single chamber mode.

19. The method of claim 5, wherein modifying the pacing parameter comprises:
   modifying a pacing mode;
   gradually decreasing a pacing rate; and
   extending an AV interval.

20. The method of claim 5, wherein modifying the pacing parameter comprises suspending left side pacing.

21. The method of claim 1, wherein characterizing the patient's supraventricular rhythm comprises characterizing the patient's supraventricular rhythm after a predetermined number of cardiac beats has been collected.

22. The method of claim 21, wherein the predetermined number is about 16.

23. The method of claim 1, wherein characterizing the patient's supraventricular rhythm, further comprises:
   providing a plurality of templates; selectively updating the plurality of templates using a plurality of the cardiac beats; and
   characterizing the patient's supraventricular rhythm using a particular template of the plurality of updated templates.

24. The method of claim 23, wherein updating the plurality of templates further comprises:
   detecting a particular cardiac beat of the plurality of cardiac beats;
   determining if the particular cardiac beat is correlated to one of the plurality of templates; and
   updating the template correlated to the particular cardiac beat.

25. The method of claim 24, wherein detecting the particular cardiac beat comprises:
   sensing rate channel signals;
   sensing shock channel signals; and
   determining if the rate channel signals and the shock channel signals meet predetermined criteria.

26. The method of claim 24, wherein determining if the particular cardiac beat is correlated to one of the plurality of templates further comprises:
   identifying a plurality of features of the template;
   aligning the shock channel signal of the particular cardiac beat and the template using a fiducial point of the template and a fiducial point of the shock channel signal of the particular cardiac beat;
   identifying a plurality of features of the shock channel signal of the particular cardiac beat; and
   using the plurality of features of the template and the plurality of features of the particular cardiac beat to determine if the beat is correlated to the template.

27. A body implantable system for characterizing a patient's supraventricular rhythm, comprising:
   a lead system, the lead system comprising electrodes extending into a heart; a detector system coupled to the lead system, the detector system configured to detect cardiac beats; and
   a control system coupled to the detector system, the control system configured to control pacing of the patient's heart, collect the cardiac beats representative of the patient's supraventricular rhythm during a plurality of periods, of which some are noncontiguous, and generate a morphology template that characterizes the patient's supraventricular rhythm using the collected cardiac beats.

28. The system of claim 27, wherein the control system is configured to modify pacing parameters and collect the cardiac beats representative of the patient's supraventricular rhythm during a time in which the pacing parameters are modified.

29. The system of claim 27, wherein the control system is configured to modify one or more pacing parameters including a pacemaker mode, a pacing rate, a pacing interval, and a pacemaker function.

30. The system of claim 29, wherein the control system is configured to store waveforms of the cardiac beats.

31. The system of claim 27, wherein the control system is configured to combine a waveform of each collected cardiac beat with waveforms of previously collected cardiac beats and to store the result of the combination.

32. The system of claim 27, wherein the control system is configured to combine a waveform of each collected cardiac beat with waveforms of previously collected cardiac beats by adding the waveform to a template waveform.

33. The system of claim 27, wherein the detector system comprises at least one rate channel amplifier coupled to the control system, the control system modifying a gain of the at least one rate channel amplifier during characterization of the patient's supraventricular rhythm.

34. The system of claim 33, wherein the gain of the at least one rate channel amplifier is not modified in response to a ventricular paced beat unless N consecutive pacing pulses have occurred since a last intrinsic ventricular beat.

35. The system of claim 34, wherein N =1, 2 or 3.

36. A system for characterizing a patient's supraventricular rhythm, comprising:

means for collecting cardiac beats during a plurality of periods, of which some are noncontiguous; and means for generating a morphology template characterizing the patient's supraventricular rhythm using the collected cardiac beats.

37. The system of claim 36, further comprising means for modifying pacing parameters.

38. The system of claim 37, wherein means for collecting the cardiac beats comprises means for collecting the cardiac beats during a time in which the pacing parameters are modified.

* * * * *